(12) United States Patent
Eckerdal et al.

(10) Patent No.: US 8,280,527 B2
(45) Date of Patent: Oct. 2, 2012

(54) SUTURE SLEEVE AND A METHOD FOR IMPLANTING ONE OR TWO LEADS INTO A VEIN

(75) Inventors: Johan Eckerdal, Knivsta (SE); Rolf Hill, Jäfälla (SE)

(73) Assignee: St. Jude Medical AB, Jarfalla (SE)

( * ) Notice: Subject to any disclaimer, the term of this patent is extended or adjusted under 35 U.S.C. 154(b) by 653 days.

(21) Appl. No.: 12/528,860

(22) PCT Filed: Mar. 26, 2007

(86) PCT No.: PCT/SE2007/000295
§ 371 (c)(1),
(2), (4) Date: Aug. 27, 2009

(87) PCT Pub. No.: WO2008/118044
PCT Pub. Date: Oct. 2, 2008

(65) Prior Publication Data
US 2010/0106170 A1    Apr. 29, 2010

(51) Int. Cl.
*A61N 1/02*    (2006.01)
(52) U.S. Cl. ........................................ 607/116; 606/232

(58) Field of Classification Search .................. 607/116, 607/149
See application file for complete search history.

(56) References Cited

U.S. PATENT DOCUMENTS

| 4,516,584 | A |  | 5/1985 | Garcia |
| 5,107,856 | A | * | 4/1992 | Kristiansen et al. ........... 607/126 |
| 5,584,874 | A |  | 12/1996 | Rugland et al. |
| 5,603,730 | A |  | 2/1997 | Romkee |
| 2012/0071833 | A1 | * | 3/2012 | Hill et al. ..................... 604/175 |

* cited by examiner

*Primary Examiner* — Carl H Layno
*Assistant Examiner* — Frances Oropeza

(57) ABSTRACT

For a suture sleeve and implantation method for one or two implantable leads, the suture sleeve is adapted to be inserted into a vein to secure and protect the lead from damage when a suture thread is positioned and tied around the vein in the region over the suture sleeve to prevent bleeding from the vein. The suture sleeve has two lead receiving through holes, into each of which a medical implantable lead is insertable. The suture sleeve also has two elongated sleeve portions, each including a lead receiving through hole, which are positioned in parallel and displaced in relation to each other such that they are connected in a connecting portion. At least one sleeve portion projects further in one direction.

6 Claims, 1 Drawing Sheet

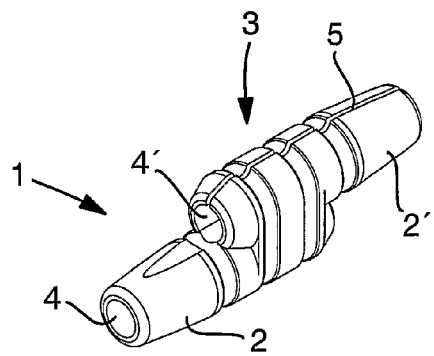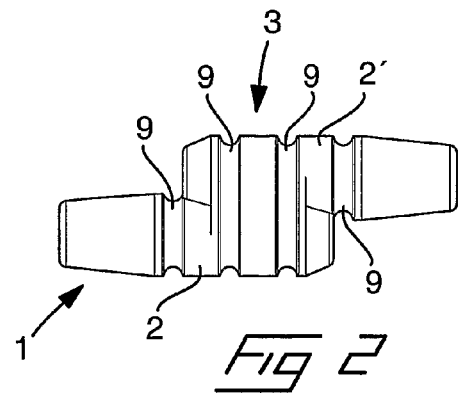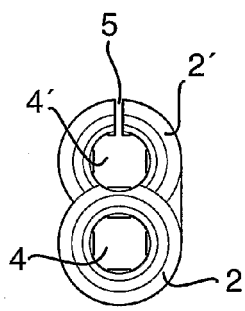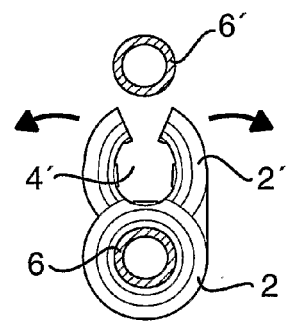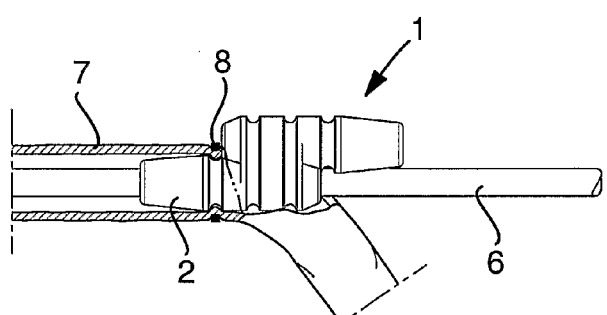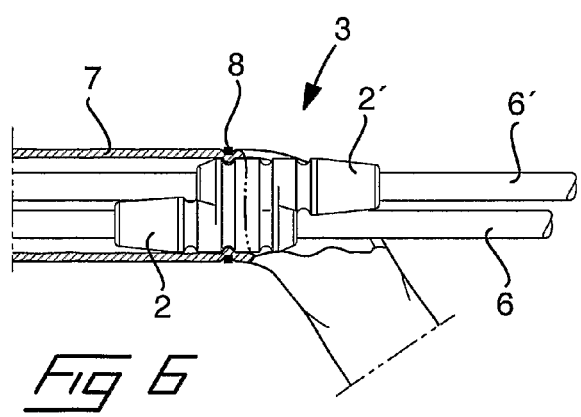

SUTURE SLEEVE AND A METHOD FOR IMPLANTING ONE OR TWO LEADS INTO A VEIN

BACKGROUND OF THE INVENTION

1. Field of the Invention

The invention relates to a suture sleeve for one or two implantable leads, the suture sleeve being adapted to be inserted into a vein to secure and protect the lead from damage when a suture thread is positioned and tied around the vein in the region over the suture sleeve to prevent bleeding from the vein, of the type having two lead receiving through holes, into each of which a medical implantable lead is insertable.

The invention also relates to a method for implanting one or two leads into a vein.

2. Description of the Prior Art

It is sometimes desirable to implant an electrical lead into a vein in an animal or human body, such that the lead extends out from the vein. This is the case e.g. when implanting a pacemaker into a body for monitoring and controlling the heart function. The pacemaker itself is implanted just under the skin in a pacemaker pocket at a suitable position, whereas one or more leads are inserted through an opening in the wall of a vein and pushed in until a distal end enters the heart where it can be attached to the heart wall.

However, the vein must be closed after lead insertion to avoid bleeding and the lead must be fixated in relation to the vein to eliminate the risk that the lead accidentally can be drawn out from its position. Avoiding bleeding is very important to prevent local hematoma since hematoma is considered as a major positive predictor for infection in the pacemaker pocket. This is accomplished by means of a suture thread, which is positioned around the vein and the lead in the area of the cut opening in the wall of the vein and which is tied around the vein and the lead. However, when closing the vein by tying the suture around the vein and the lead, there is a risk that the lead might get damaged by squeezing of the suture thread around the lead if the suture is made too tight. The suture stress will be concentrated to a small area and may cause intensive abrasion load to the lead body. On the other hand, if the suture is not tight enough, bleeding may occur and cause hematoma. If the suture is not combined with fixation of the lead elsewhere, there is also a risk for longitudinal lead movement and lead dislodgment if the suture is not sufficient tight.

To eliminate these risks it is known to use a so called suture sleeve, which is positioned around the lead in the area of the lead-through in the wall of the vein. In this way the suture sleeve will protect the lead from damage by the suture thread and the suture sleeve will fixate the lead in a sufficient degree.

However, sometimes it is desirable to connect the pacemaker with the heart by means of two separate leads. In such a case it is common practice to tying the suture around the vein directly onto unprotected leads to prevent from bleeding. The leads are then fixated separately some distance from the vein entrance by using the suture sleeves to prevent from longitudinal lead movement and lead dislodgement. This has effect that the leads in the venous entrance, where they are unprotected from the suture thread, may become damaged.

U.S. Pat. No. 5,107,856 discloses a suture sleeve for two leads. The suture sleeve is formed as a flexible strip having two spaced apart lead receiving channels. During use, one lead is positioned in each of the lead receiving channels and then the flexible strip is wrapped around the leads. Finally, the suture sleeve is positioned in the cut opening in the vein and tied around by a suture thread.

However, there are several disadvantages with such a suture sleeve. For example, it is not possible to position and fixate only one lead in a suture sleeve, which is adapted for two leads, since then blood will leak out through the channel which has no lead positioned therein. I.e. when using a suture sleeve being adapted for two leads into a vein it is necessary to insert two leads. Otherwise, bleeding will occur. Accordingly, it is necessary to keep in stock suture sleeves adapted for one as well as for two leads to be prepared for different applications.

Moreover, the leads in question are very small, having a cross sectional dimension of only about 2 mm, which has to effect that also the suture sleeve will be very small. This will have to result that it will be very difficult to wrap around the leads properly with the suture sleeve, insert it through the opening in the vein and fixate the assembly by means of a suture thread without losing the suture sleeve during the handling. With a suture sleeve according to the aforementioned patent it is also impossible to completely eliminate bleeding since, as is evident from the drawings in the document, there will always remain some gaps between the leads and the suture sleeve in an assembled state.

SUMMARY OF THE INVENTION

It is an object of the invention to overcome the disadvantages with prior art suture sleeves. More precisely it is an object to provide a suture sleeve for one or two electrical leads which is easy to handle and by means of which it is possible to effectively eliminate any bleeding independently of whether there are leads positioned in both through holes or not.

The invention also relates to a method for implanting one or two electrical leads into a vein of a human or animal body, having essentially the same object as above.

The basis of the invention is the insight that the above object may be achieved by means of a suture sleeve having two elongated sleeve portions, each including a lead receiving through hole. The suture sleeve portions are displaced in relation to each other and connected in parallel at a connecting portion such that one sleeve portion is projecting further than the other in one direction. With a suture sleeve formed in this way it is possible to implant only one lead into the vein, in which case only the projecting part or the sleeve portion is inserted into the vein and tied around with a suture thread. Bleeding through the hole in the sleeve portion, which is not occupied by a lead, is then prevented since that sleeve portion is not inserted into the vein but is located entirely outside of the vein. When, on the other hand, it is desirable to implant two leads in the vein, both leads are positioned in a respective through hole and the suture sleeve is inserted into the vein, so far such that the connecting portion is positioned into the vein, and a suture thread is tied around the vein in the region of the connecting portion.

Within this general idea, the invention can be modified in many different ways. In a hereinafter described and in the drawings illustrated embodiment of the invention, the two sleeve portions have equal lengths which has to effect that the sleeve portions will project in different directions and an optional end of the suture sleeve can be used for insertion into the vein. However, it is also possible to form the sleeve portions with different lengths in which case the longer sleeve portion will project in one direction, whereas the sleeve portions can be aligned in the other end.

In a hereinafter described and illustrated embodiment, the suture sleeve is formed of an elastic material and such that one through hole is unbroken and adapted to be pre-assembled onto one of the electrical leads, whereas the other hole is provided with a longitudinal slot such that the material around the hole can be deflected for widening the slot and inserting a lead sideways into the hole through the widened slot.

BRIEF DESCRIPTION OF THE DRAWINGS

FIG. 1 is a perspective view of a suture sleeve according to the invention.

FIG. 2 is a side view of the suture sleeve of FIG. 1.

FIG. 3 is an end view of the suture sleeve of FIGS. 1 and 2.

FIG. 4 is an end view according to FIG. 3, with the material around a slot in one of the through holes deflected outwardly.

FIG. 5 is a perspective view of the suture sleeve being inserted into a vein in a first position, in which only one electrical lead is inserted into the suture sleeve and the vein.

FIG. 6 is a perspective view of the suture sleeve being inserted into a vein in a second position, in which two electrical leads are inserted into the suture sleeve and the vein.

DESCRIPTION OF THE PREFERRED EMBODIMENTS

Reference is first made to FIGS. 1 to 3, in which a suture sleeve 1 according to the invention is illustrated in a perspective view, a side view and an end view, respectively. The suture sleeve comprises two sleeve portions 2, 2', having equal lengths, which are interconnected and positioned in parallel at a connecting portion 3 and displaced in relation to each other such that one of the sleeve portions is projecting from one end of the connecting portion 3, while the other sleeve portion is projecting from the other end.

Each of the sleeve portions 2, 2' are formed of an elastic material and has a lead receiving through hole 4, 4' in the longitudinal direction. As is best seen in FIG. 3, one of the through holes 4 is unbroken, while the other through hole 4' is provided with a slot 5 in the longitudinal direction. The reason for this is that the unbroken through hole 4 is adapted to be pre-assembled onto an electrical lead 6, as is illustrated in FIG. 4, to prevent losing of the suture sleeve e.g. during an implantation. The other through hole 4' is adapted for insertion of a lead 6' into the through hole sideways when desired, by deflecting the material around the slot 5 and widening it.

Now reference is made to FIG. 5, in which is illustrated the use of the suture sleeve 1 for implanting one single lead 6 into a vein 7. The lead 6 is inserted into the through hole 4 in the sleeve portion 2 which is unbroken and not provided with any slot 5. Preferably the lead 6 and the suture sleeve can be delivered pre-assembled together with the lead 6 inserted into the unbroken through hole 4. Since only one lead is inserted into the suture sleeve, only the suture portion 2 accommodating the lead 6, is inserted into an opening in the vein 7 and a suture thread 8 is positioned and tied around the vein and the projecting suture portion, for securing the suture sleeve in relation to the vein and to prevent bleeding. Since no lead is inserted into the through hole 4' in the other sleeve portion 2', bleeding would have occurred through that hole if the sleeve portion 2' had been inserted into the vein. Due to the design of the suture sleeve according to the invention, it is possible, as is illustrated in the drawing, to insert only the projecting part of the sleeve portion 2 into the vein and to leave the other sleeve portion 2' outside of the vein.

FIG. 6 illustrates the case when a lead 6, 6' is inserted in both of the through holes in the sleeve portions 2, 2', respectively. The hole 4 can be preassembled onto the lead 6, whereas the lead 6' can be introduced into the hole 4' by deflecting the material around the hole and widening the slot 5 such that the lead can be inserted sideways. In this case both of the sleeve portions 2 and 2' is inserted into the opening in the vein 7, i.e. also the connecting portion 3. Accordingly, the suture thread 8 is positioned and tied around the vein and the connecting portion 3 of the suture sleeve. To improve the securing of the suture sleeve in relation to the vein, the suture sleeve is provided with circumferential grooves 9 around the outer periphery of both the projecting part of each sleeve portion 2, 2' as well as the connecting portion 3. In this way the suture thread as well as vein tissue may sink into a groove when tying the suture thread around the vein, which will create a better grip around the suture sleeve.

Although modifications and changes may be suggested by those skilled in the art, it is the intention of the inventors to embody within the patent warranted heron all changes and modifications as reasonably and properly come within the scope of their contribution to the art.

We claim as our invention:

1. A suture sleeve for selectively introducing one or two implantable leads in vivo into a vein, said suture sleeve comprising:
    a suture sleeve body comprising two elongated sleeve portions each having a through-hole therein configured to receive a medical lead therethrough inserted therein in a longitudinal direction, said elongated sleeve portions being disposed side-by-side and said sleeve body comprising a connecting portion that connects said sleeve portions with each other;
    one of said sleeve portions projecting further in said longitudinal direction than the other of said sleeve portions;
    said sleeve portions and said sleeve body being configured to allow, when only one lead is inserted into one through hole of one of said sleeve portions, only said one of said sleeve portions to be inserted into the vein and tied around by a suture thread, with said other sleeve portion being positioned outside of said vein and, when medical leads are inserted respectively into each of the through-holes of said two sleeve portions, said sleeve body being configured to be inserted, with both of said sleeve portions and said connecting portion, into said vein and tied around by a suture thread; and
    said sleeve body being configured, when either one or both of said sleeve portions has a medical lead inserted in the through-hole thereof, to prevent bleeding from the vein when tied around with a suture thread.

2. A suture sleeve as claimed in claim 1 wherein said sleeve portions are of equal length.

3. A suture sleeve as claimed in claim 1 wherein said sleeve body is formed of an elastic material and comprises a slot in said insertion direction allowing material around at least one of said through holes to be deflected, to widen said slot and allow introduction of a medical lead sideways into said through hole, perpendicular to said insertion direction.

4. A suture sleeve as claimed in claim 3 wherein only one of said sleeve portions comprises said slot.

5. A method for selectively introducing one or two implantable leads in vivo into a vein using a suture sleeve, comprising the steps of:
    providing a suture sleeve body comprising two elongated sleeve portions each having a through-hole therein configured to receive a medical lead therethrough inserted therein in a longitudinal direction, said elongated sleeve portions being disposed side-by-side and said sleeve body comprising a connecting portion that connects said sleeve portions with each other, one of said sleeve portions projecting further in said insertion direction than the other of said sleeve portions;

when only one lead is inserted into one through hole of one of said sleeve portions, inserting only said one of said sleeve portions into the vein and tying the sleeve body around with a suture thread, with said other sleeve portion being positioned outside of said vein and, when medical leads are inserted respectively into each of the through-holes of said two sleeve portions, inserting both of said sleeve portions and said connecting portion, into said vein and tying said sleeve body around with a suture thread.

6. A method as claimed in claim 5 comprising:

forming said suture sleeve body of elastic material with a slot in one of said through holes; and inserting a medical lead in said one of said through holes by deflecting said material around said slot to widen said slot and inserting the medical lead into the through hole through the widened slot.

* * * * *